(12) United States Patent
Lai et al.

(10) Patent No.: US 11,576,993 B2
(45) Date of Patent: Feb. 14, 2023

(54) ULTRAVIOLET AIR GERMICIDAL LAMP SYSTEM

(71) Applicant: DELTA ELECTRONICS, INC., Taoyuan (TW)

(72) Inventors: Pin-Chen Lai, Taoyuan (TW); Chih-Hsien Wang, Taoyuan (TW); Kuan-Hsien Tu, Taoyuan (TW)

(73) Assignee: DELTA ELECTRONICS, INC., Taoyuan (TW)

( * ) Notice: Subject to any disclaimer, the term of this patent is extended or adjusted under 35 U.S.C. 154(b) by 0 days.

(21) Appl. No.: 17/242,228

(22) Filed: Apr. 27, 2021

(65) Prior Publication Data
US 2022/0111106 A1   Apr. 14, 2022

(30) Foreign Application Priority Data
Oct. 14, 2020   (TW) .................................. 109213451

(51) Int. Cl.
*A61L 9/20*   (2006.01)

(52) U.S. Cl.
CPC ............. *A61L 9/20* (2013.01); *A61L 2209/12* (2013.01)

(58) Field of Classification Search
None
See application file for complete search history.

(56) References Cited

U.S. PATENT DOCUMENTS

| | | | |
|---|---|---|---|
| 10,316,141 B2 * | 6/2019 | Niemiec | F21V 33/0096 |
| 2013/0094204 A1 * | 4/2013 | Budai | A61L 9/205 362/230 |
| 2015/0064069 A1 * | 3/2015 | Yi | A61L 9/20 422/121 |
| 2019/0292315 A1 * | 9/2019 | Niemiec | C08G 81/00 |
| 2020/0062622 A1 * | 2/2020 | Linley | C02F 1/583 |
| 2022/0090778 A1 * | 3/2022 | Chung | F24F 8/22 |

FOREIGN PATENT DOCUMENTS

| | | | | |
|---|---|---|---|---|
| CN | 1317040 C | | 5/2007 | |
| DE | 102014012870 A1 * | | 3/2015 | ............ A61L 9/20 |
| FR | 3010907 A1 * | | 3/2015 | ............ A61L 9/16 |
| KR | 101373192 B1 * | | 3/2014 | |
| TW | M540252 U | | 4/2017 | |
| TW | M560566 U | | 5/2018 | |
| WO | WO-2012068569 A1 * | | 5/2012 | ............ A61L 9/20 |

\* cited by examiner

*Primary Examiner* — Andrew Smyth
(74) *Attorney, Agent, or Firm* — CKC & Partners Co., LLC (57) ABSTRACT

An ultraviolet air germicidal lamp system includes a base frame including an air inlet and an air outlet, an ultraviolet germicidal module on the base frame, and a lamp module in the base frame. The ultraviolet germicidal module includes a fan, an inlet duct, an ultraviolet lamp module including a cavity and ultraviolet lamps in the cavity, and an outlet duct. The fan is connected to the air inlet. The intake of the cavity of the ultraviolet lamp module is connected to the fan by the inlet duct. The vent of the cavity of the ultraviolet lamp module is connected to the air outlet by the outlet duct. The body diameter of the cavity is larger than the diameters of the inlet duct and the outlet duct.

20 Claims, 11 Drawing Sheets

ULTRAVIOLET AIR GERMICIDAL LAMP SYSTEM

CROSS-REFERENCE TO RELATED APPLICATION

This application claims priority to Taiwan Application Serial Number 109213451, filed on Oct. 14, 2020, which is herein incorporated by reference in its entirety.

BACKGROUND

Field of Invention

The present disclosure relates to ultraviolet air germicidal system.

Description of Related Art

The ultraviolet (UV) sterilization may be performed for sterilizing of the pathogen and decreasing the possibility of reinfection. Except for being applied on the objects, the UV sterilization may be applied on the pathogen transmitted in air. The air sterilization effect is implemented usually by direct irradiation of the UV lamps toward the air with natural convection of the air in an enclosed space. However, the UV lamps are operated in a vacant space to avoid UV irradiation on human body, which indirectly decreases the efficiency of the UV sterilization.

SUMMARY

The disclosure provides an ultraviolet air germicidal lamp system including a base frame with an air inlet and an air outlet, an ultraviolet germicidal module on the base frame, and a lamp module disposed in the base frame. The ultraviolet germicidal module includes a fan connected to the air inlet, an ultraviolet lamp module including a cavity with an intake and a vent and a plurality of ultraviolet lamps disposed in the cavity, an inlet duct connecting the intake of the cavity and the fan, and an outlet duct connecting the vent of the cavity and the air outlet, in which a body diameter of the cavity is larger than the diameters of the intake and the vent.

It is to be understood that both the foregoing general description and the following detailed description are by examples, and are intended to provide further explanation of the disclosure as claimed.

BRIEF DESCRIPTION OF THE DRAWINGS

The disclosure can be more fully understood by reading the following detailed description of the embodiment, with reference made to the accompanying drawings as follows. It is noted that, in accordance with the standard practice in the industry, various features are not drawn to scale.

FIG. 2A to FIG. 2G illustrate schematic top views of the UV germicidal lamp systems according to some embodiments of this disclosure.

DETAILED DESCRIPTION

The UV sterilization is common for the locations with pathogen, such as hospitals, due to its simple and fast operation. If the pathogen may be transmitted by air, it may be sterilized by the UV rays. The UV sterilization of the air usually includes the direct irradiation to the air in the environment, or purifying the air by ozone generated from oxygen excitation with the UV rays. However, the direct irradiation of the UV lamps or the generation of ozone leads to the limitation of a sterilizing environment without human body. In addition, the sterilizing space is often enclosed to avoid the transmission of the pathogen, and the air sterilization is completed slowly by natural convection in the space.

The present disclosure provides an UV air germicidal lamp system including a base frame, a UV germicidal module on the base frame, and a lamp module disposed in the base frame. The UV rays leakage may be prevented during the working of the UV air germicidal lamp system by the closed track of the UV germicidal module. This allows operating the UV air germicidal lamp system in a condition with human body, which increases the UV sterilization efficiency.

Furthermore, the UV air germicidal lamp system has already included the lamp module. As a result, it may be integrated with the current light fixtures. The UV air germicidal lamp system may be directly installed in the position of the original light fixture without additional changing of the indoor layout, and its installation is also convenient. The UV air germicidal lamp system provided by the present disclosure would be described with the following various embodiments.

Figure 1A:
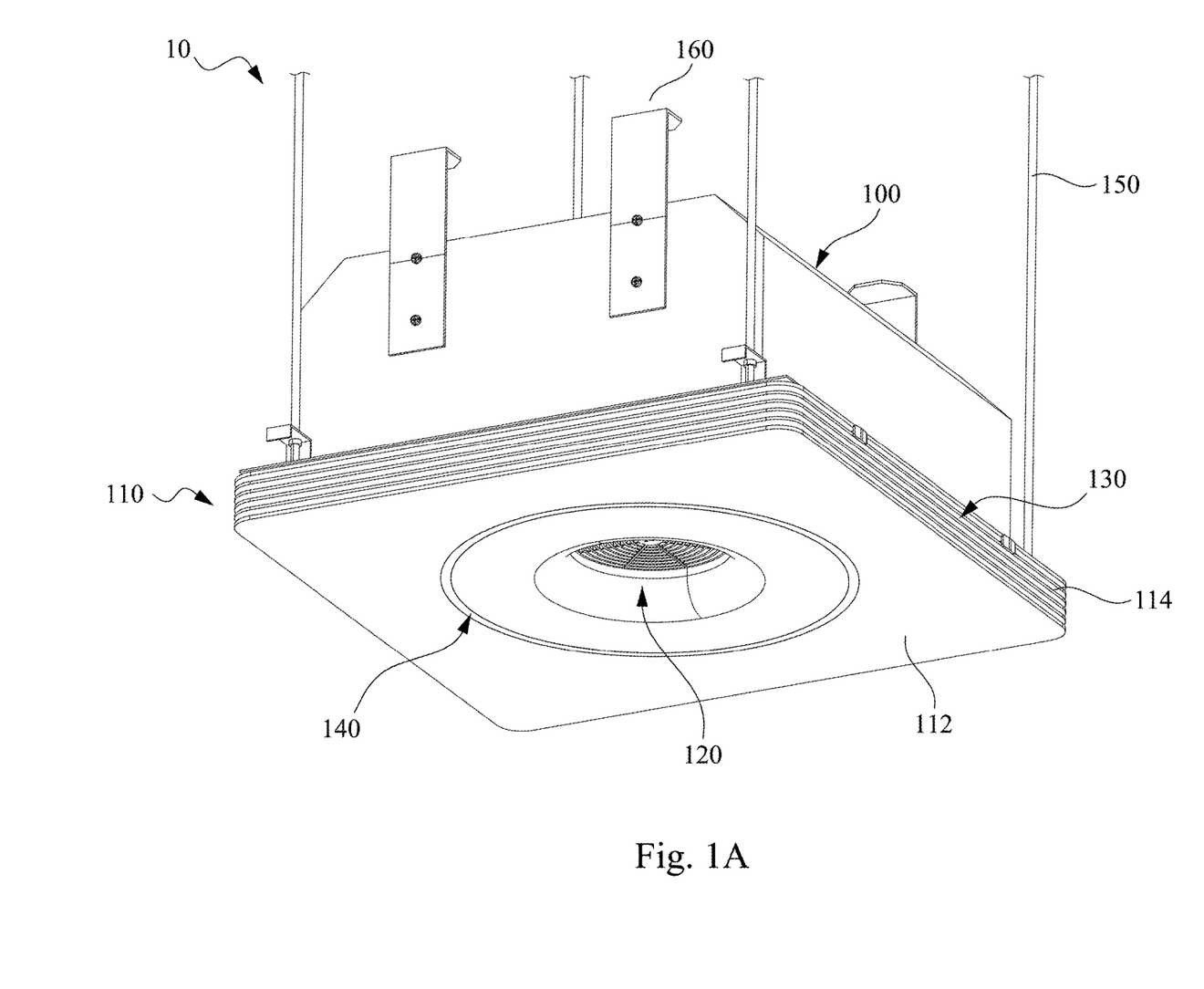
FIG. 1A illustrates an exterior perspective view of the UV air germicidal lamp system according to some embodiments of this disclosure.
Figure 1B:
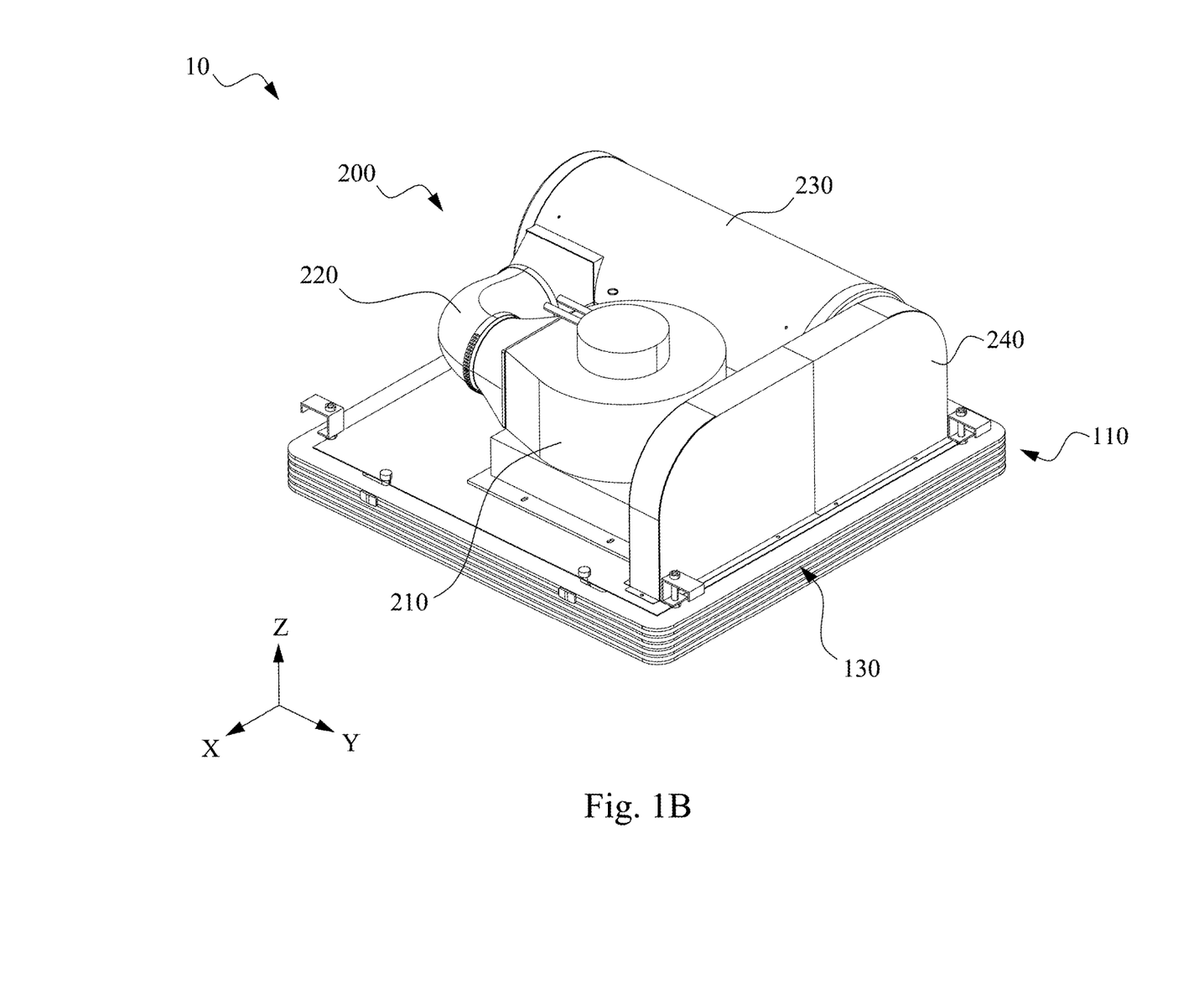
FIG. 1B illustrates an interior perspective view of the UV air germicidal lamp system in FIG. 1A according to some embodiments of this disclosure.

Referring to FIG. 1A to FIG. 1D, FIG. 1A illustrates an exterior perspective view of the UV air germicidal lamp system 10 according to some embodiments of this disclosure, and FIG. 1B illustrates an interior perspective view of the UV air germicidal lamp system 10. Specifically, FIG. 1B is the perspective view of the UV air germicidal lamp system 10 without the case 100. According to some alternative embodiments of the UV air germicidal lamp system 10, FIG. 1C and FIG. 1D respectively illustrates a perspective view of the UV air germicidal lamp system.

As shown in FIG. 1A and FIG. 1B, the UV air germicidal lamp system 10 includes a case 100, a base frame 110, a UV germicidal module 200, and a lamp module 140. In some embodiments, the case 100 may be disposed on the base frame 110 to together form a storage space for the UV germicidal module 200. The lamp module 140 may be disposed in the base frame 110, which the lamp module 140 and the UV germicidal module 200 are disposed on the opposite sides of the base frame 110. Therefore, the lamp module 140 may be exposed by the base frame 110 to provide indoor illumination, while the UV germicidal module 200 may be hidden on the other side of the base frame 110 to sterilize the indoor air.

In some embodiments, the base frame 110 includes a bottom surface 112 with an air inlet 120 and side surfaces 114 with an air outlet 130. The indoor air flows into the UV germicidal module 200 through the air inlet 120 and leaves the UV germicidal module 200 through the air outlet 130 after sterilization. The air inlet 120 and the air outlet 130 are arranged on different surfaces of the base frame 110 so that the decreasing of the sterilization effect, due to the mixing of the air before and after sterilization, may be prevented.

In some embodiments, the air inlet 120 may be designed with a streamlined shape such as a funnel to increase the air amount flowing into the UV air germicidal lamp system 10 and to decrease the air resistance. The air outlet 130 may be disposed on the side surface 114 of the base frame 110 so that the air after sterilization laterally leaves the UV air germicidal lamp system 10, which avoids the discomfort caused by the air blowing directly toward human body.

In some embodiments, the air outlet 130 may be fence-shaped to uniform the air leaving the UV air germicidal lamp system 10. In some embodiments, the air outlet 130 may be only disposed on one side surface 114. In some other embodiments, the air outlet 130 may be disposed on two or more side surfaces 114.

In some embodiments, the UV germicidal module 200 includes a fan 210, an inlet duct 220, a UV lamp module 230, and an outlet duct 240. The fan 210 is connected to the air inlet 120 on the base frame 110 so that it may drive the air flowing into the UV germicidal module 200 under operation, which accelerates the air convection in the environment and increases the sterilization efficiency.

In some embodiments, the fan 210 may be a centrifugal fan including an intake on the Z-axis direction and a vent on the Y-axis direction, and it may generate high wind pressure to overcome high wind resistant. The perpendicular flow direction and the high wind pressure may increase the arrangement manners of the subsequent track. The air flowing into the UV germicidal module 200 may flow in an expected direction because of the fan 210, which prevents the mixing of the air before and after sterilization and the decreasing of the sterilization efficiency.

The UV lamp module 230 and the fan 210 are connected by the inlet duct 220, and the UV lamp module 230 and the air outlet 130 are connected by the outlet duct 240. As shown in FIG. 1B, the inlet duct 220 is connected to the side surface of the UV lamp module 230, while the outlet duct 240 is connected to the bottom surface of the UV lamp module 230 perpendicular to the side surface. However, the inlet duct 220 may be connected to the bottom surface of the UV lamp module 230, and the outlet duct 240 may be connected to the side surface of the UV lamp module 230. The two ends of the UV lamp module 230 are connected to the inlet duct 220 and the outlet duct 240, respectively. Therefore, the leakage of the UV rays in the UV lamp module 230 may be prevented so that the UV germicidal module 200 may be operated in the space with human body.

The UV lamp module 230 is an individual module, that is, the operation, replacement, and maintenance of the UV lamp module 230 may be completed separately without affecting other modules in the UV air germicidal lamp system 10, such as the lamp module 140.

The inlet duct 220 may concentrate the air before sterilization and send the air into the following UV lamp module 230. In some embodiments, the inlet duct 220 may include the spoilers that uniform the air before sterilization through the inlet duct 220.

The outlet duct 240 may decrease the wind pressure of the air after sterilization so that the air may smoothly leave the UV germicidal module 200. In some embodiments, as shown in FIG. 1B, the outlet duct 240 may include the fillet at the upper portion so that the flow may smoothly leave the outlet duct 240 without accumulating in the outlet duct 240. In some embodiments, the flow speed at the connection part between the outlet duct 240 and the UV lamp module 230 may be different from the flow speed in the outlet duct 240 far from the UV lamp module 230. The fillet at the upper portion of the outlet duct 240 may guide the flow in the outlet duct 240 to rapidly leave the UV lamp module 230.

Figure 1C:
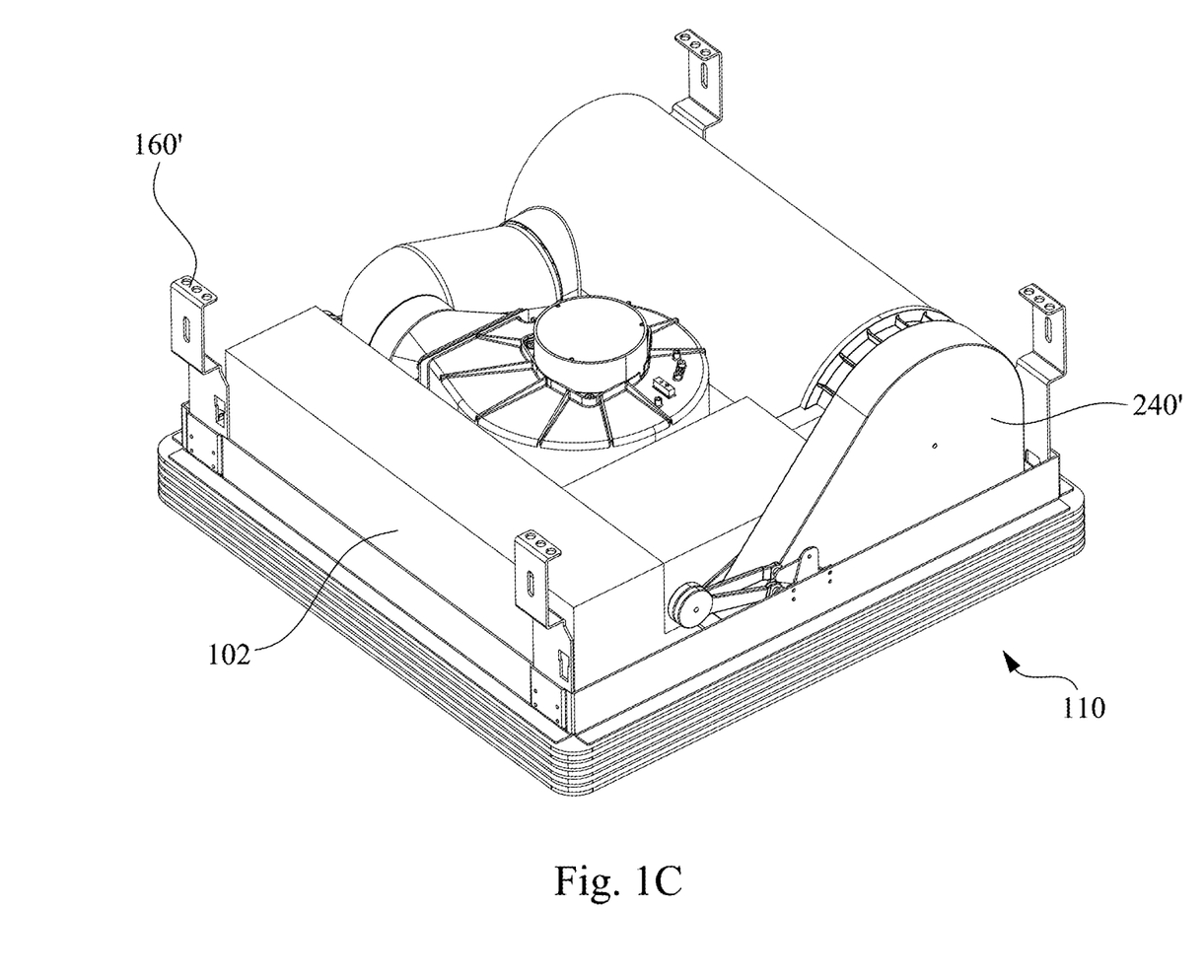
FIG. 1C illustrates a perspective view of the UV air germicidal lamp system according to some embodiments of this disclosure.

In some other embodiments, as shown in FIG. 1C, the cross-sectional area of the outlet duct 240' parallel to the base frame 110 may include an area gradient along the height direction of the outlet duct 240'. For example, the cross-sectional area of the outlet duct 240' parallel to the base frame 110 may gradually reduces from a side adjacent to the base frame 110, which leads to a wide-bottom and narrow-top shape of the outlet duct 240'. This also drives the flow in the outlet duct 240' to flow toward the air outlet, such as the air outlet 130 in FIG. 1B.

The outlet duct 240 is connected to the air outlet 130 so that the air after sterilization may leave the UV germicidal module 200 through the outlet duct 240. In some embodiments, the outlet duct 240 may include the inner spoilers that uniform the air after sterilization through the outlet duct 240. In some embodiments, the outlet duct 240 may be connected to the air outlet 130 on one side surface 114 of the base frame 110, or the outlet duct 240 may be connected to the air outlet 130 on more than one side surfaces 114 of the base frame 110.

The lamp module 140 is disposed at the bottom surface 112 of the base frame 110 for daily illumination. The lamp module 140 is an individual module, that is, the operation, replacement, and maintenance of the lamp module 140 may be completed separately without affecting other modules in the UV air germicidal lamp system 10, such as the UV lamp module 230.

The lamp module 140 may include illumination elements disposed in the base frame 110, for example, LED panel, LED tube, or other suitable elements providing light source. The lamp module 140 may include illumination region exposed by the bottom surface 112. As shown in FIG. 1A, the lamp module 140 may include an arc illumination region surrounding the air inlet 120. In some embodiments, the lamp module 140 may include the illumination region with other shapes and arrangements.

According to some embodiments, as shown in FIG. 1A, the UV air germicidal lamp system 10 may further include suspension lines 150 connected to the base frame 110 or suspension brackets 160 connected to the case 100. The suspension line 150 may suspend the UV air germicidal lamp system 10 at the ceiling, while the position of the base frame 110 may match the original ceiling board. The suspension bracket 160 may be installed onto the light steel joist ceiling to further stabilize the UV air germicidal lamp system 10.

In some other embodiments, as shown in FIG. 1C, the UV air germicidal lamp system 10 may further include a mounting bracket 160' connected to the base frame 110. The UV air germicidal lamp system 10 may be installed onto the light steel joist ceiling by the mounting bracket 160'. Alternatively, a suspension line, such as suspension line 150 in FIG.

1A, may be connected to the mounting bracket 160' to suspend the UV air germicidal lamp system 10 at the ceiling.

In some embodiments, as shown in FIG. 1A and FIG. 1B, the fan 210, the inlet duct 220, the UV lamp module 230, and the outlet duct 240 of the UV germicidal module 200 are disposed in the storage space formed by the case 100 and the base frame 110. In some embodiments, the UV germicidal module 200 may not be entirely disposed in the storage space between the case 100 and the base frame 110.

According to some alternative embodiments, as shown in FIG. 1C, the case 102 is disposed on the base frame 110, and the UV germicidal module 200 may be entirely disposed outside of the storage space formed by the case 102 and the base frame 110. Other components of the UV air germicidal lamp system 10 may be disposed in the storage space formed by the case 102 and the base frame 110, such as wires (not shown).

Figure 1D:
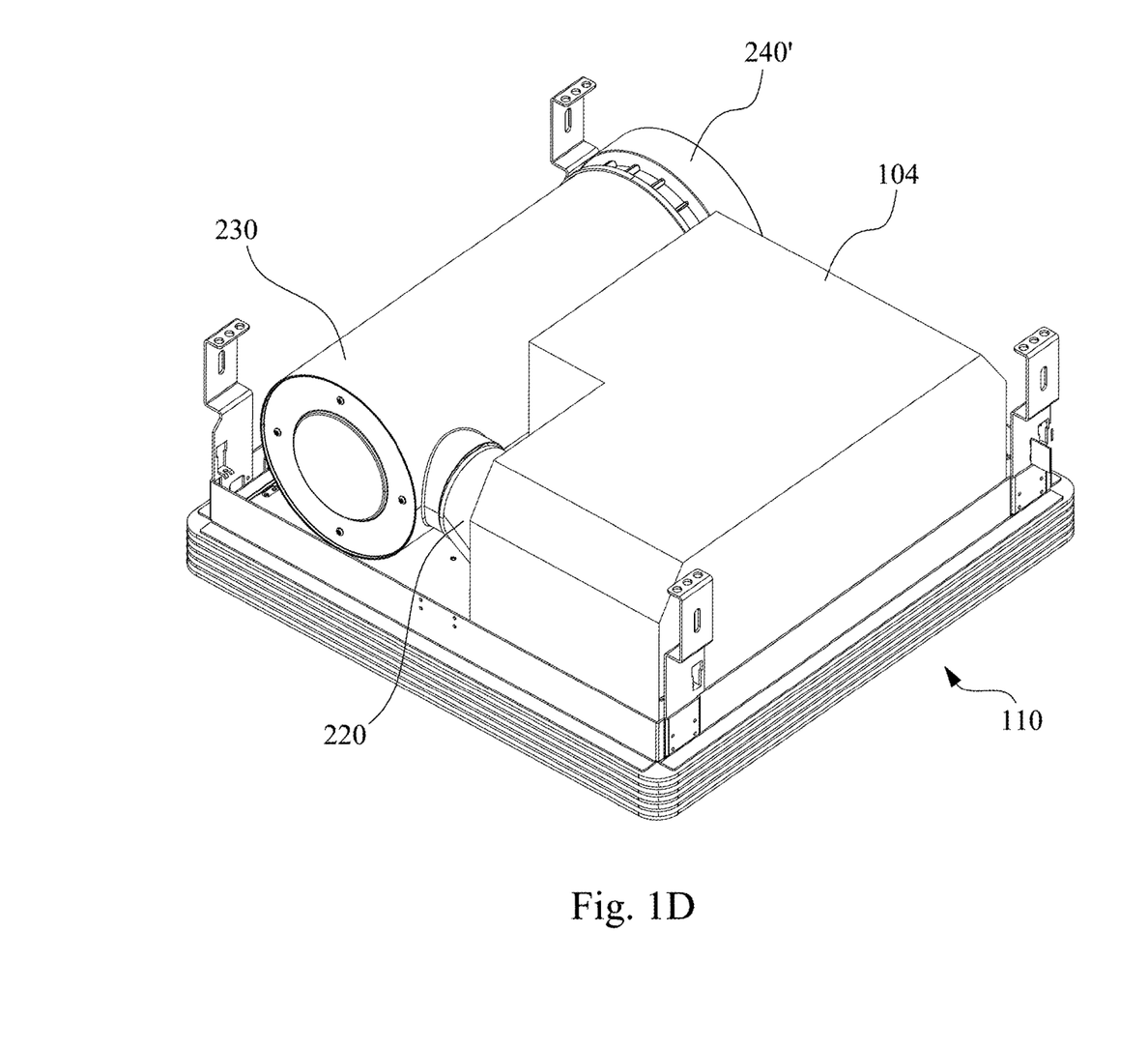
FIG. 1D illustrates a perspective view of the UV air germicidal lamp system according to some embodiments of this disclosure.

According to some alternative embodiments, as shown in FIG. 1D, the case 104 is disposed on the base frame 110. The fan (not shown) of the UV germicidal module 200 may be disposed in the storage space formed by the case 104 and the base frame 110, the inlet duct 220 may connect the fan and the UV lamp module 230 from inside to outside of the storage space, and the UV lamp module 230 and the outlet duct 240' may be disposed outside of the storage space.

Referring to FIG. 1A and the above mentioned description, the suspended UV air germicidal lamp system 10 may include the UV germicidal module 200 hidden by the ceiling and the base frame 110 exposed by the ceiling. This reduces additional changing of the original indoor layout and improves the convenience of installation. In some embodiments, the arrangement of the components of the UV germicidal module 200 relative to the ceiling board may be adjusted according to the indoor layout and the application of the UV air germicidal lamp system 10, which would be discussed in detail.

Figure 2A:
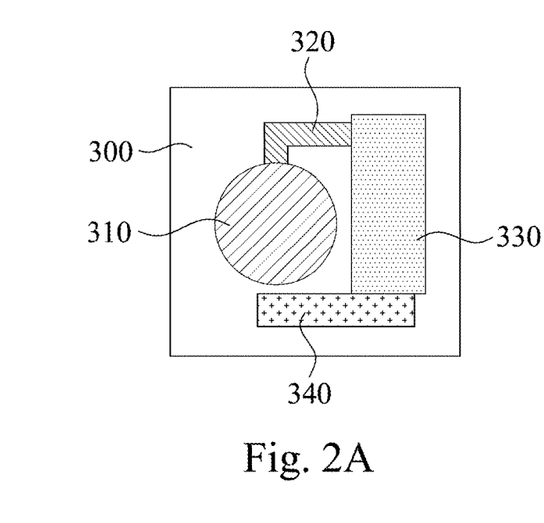
Figure 2B:
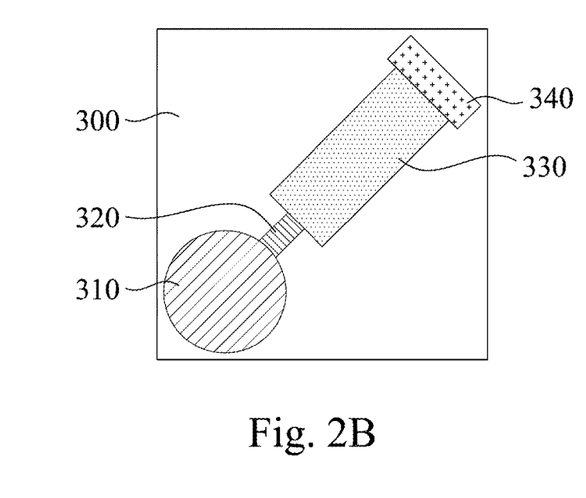
Figure 2C:
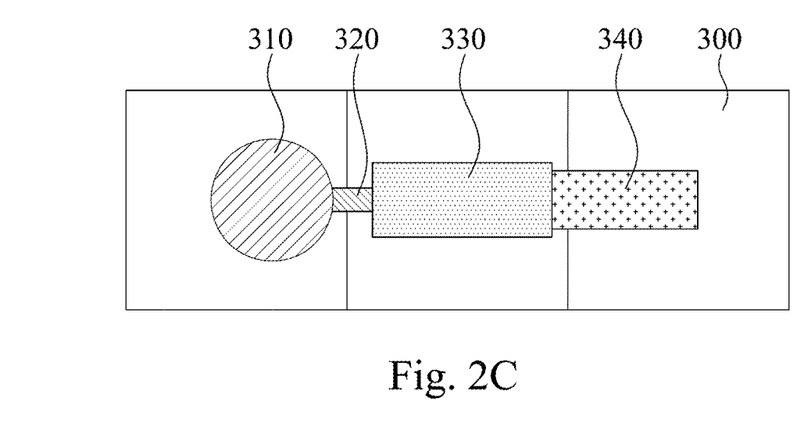

According to some embodiments of the disclosure, FIG. 2A to FIG. 2C illustrate schematic top views of the UV germicidal lamp systems including the fan 310, the inlet duct 320, the UV lamp module 330, and the outlet duct 340. It should be noted that the position of the fan 310 corresponds to the air inlet (not shown) of the UV air germicidal lamp system, and that the position of the outlet duct 340 corresponds to the air outlet (not shown) of the UV air germicidal lamp system. Although only the fan 310 and the outlet duct 340 are illustrated in FIG. 2A to FIG. 2C, the fan 310 and the outlet duct 340 may thus represent the position of the air inlet and the air outlet.

In some embodiments, the air inlet, the UV lamp module 330, and the air outlet may be disposed on the same or different ceiling boards 300. In the embodiments of FIG. 2A and FIG. 2B, the fan 310, the inlet duct 320, the UV lamp module 330, and the outlet duct 340 are arranged in a single ceiling board 300. In other words, the air inlet, the UV lamp module 330, and the air outlet may be arranged in single ceiling board 300. In the embodiment of FIG. 2C, the fan 310, the inlet duct 320, the UV lamp module 330, and the outlet duct 340 are arranged in different ceiling boards 300. In other words, the air inlet, the UV lamp module 330, and the air outlet may be arranged in different ceiling boards 300, while the UV lamp module 330 is disposed between the air inlet and the air outlet spaced apart from each other.

According to some embodiments of the disclosure, the components of the UV air germicidal lamp system may include different arrangements. As shown in FIG. 2A, the inlet duct 320, the UV lamp module 330, and the outlet duct 340 may be arranged as a spiral shape to reduce the volume of the UV germicidal module and the UV air germicidal lamp system. In some other embodiments, as shown in FIG. 2B and FIG. 2C, the inlet duct 320, the UV lamp module 330, and the outlet duct 340 may be arranged as a non-spiral shape, such as a linear shape, while the UV lamp module 330 is disposed between the air inlet and the air outlet. In other embodiments, the UV germicidal module may include more than one UV lamp module 330, which would not be discussed here in detail.

Figure 3:
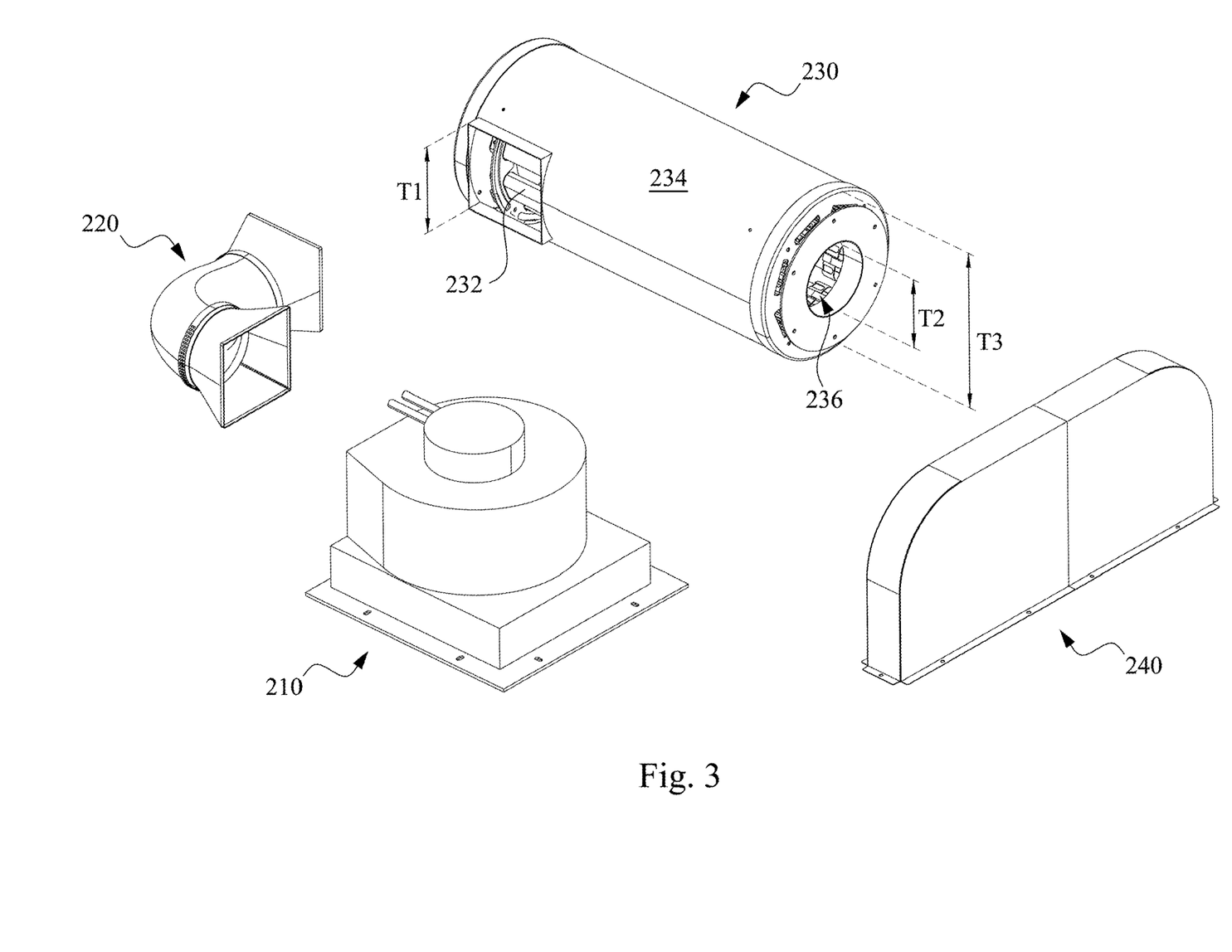
FIG. 3 illustrates an exploded view of the UV germicidal module according to some embodiments of this disclosure.

According to some embodiments, FIG. 3 illustrates an exploded view of the UV germicidal module 200 in FIG. 1B including the fan 210, the inlet duct 220, the UV lamp module 230, and the outlet duct 240. As shown in FIG. 3, the UV lamp module 230 includes a cavity 234 and UV lamps disposed in the cavity 234. The cavity 234 has an intake 232 and a vent 236, in which the intake 232 has a diameter T1 smaller than a body diameter T3 of the cavity 234, and the vent 236 has a diameter T2 smaller than the body diameter T3 of the cavity 234. In some embodiments, the body diameter T3 of the cavity 234 may be at least twice larger than the diameter T1 of the intake 232 and the diameter T2 of the vent 236.

As a result of the larger body diameter T3 of the cavity 234 compared to the diameter T1 of the intake 232 and the diameter T2 of the vent 236, the flow speed of the air may vary due to the changed cross-sectional area of the track vertical to the flow. More specifically, the flow speed of the air may change when the air flows into the UV lamp module 230 through the inlet duct 220 and leaves the UV lamp module 230 through the outlet duct 240. The air is then retained in the UV lamp module 230 so that it extends the air retention time in the UV lamp module 230. Therefore, the retained air may be sufficiently sterilized by the UV lamp module 230, which increases the sterilization efficiency of the UV germicidal module 200.

Figure 4:
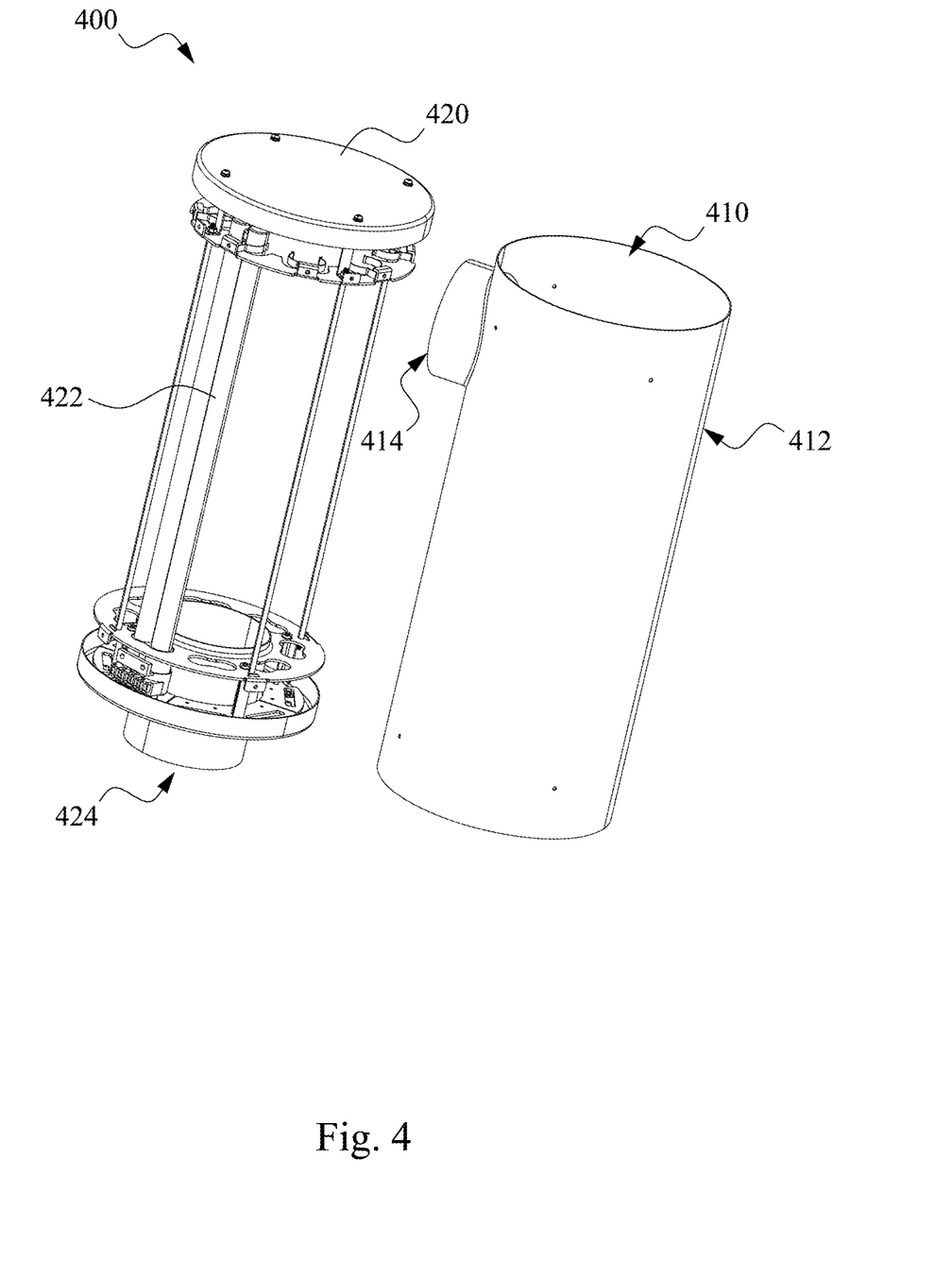
FIG. 4 to FIG. 6 illustrate exploded views of the UV lamp modules according to various embodiments of this disclosure.

According to some embodiments, FIG. 4 illustrates an exploded view of the UV lamp module 400. The UV lamp module 400 is similar to the UV lamp module 230 in FIG. 1B and may be applied in the UV air germicidal lamp system 10.

The UV lamp module 400 includes a cavity 410 formed by a shell 412 and an inner column 420 in the cavity 410. In some embodiments, the shell 412 may be a hollow structure. In some embodiments, the cavity 410 may be a cylindrical cavity to concentrate the UV rays of the UV lamp module 400 and to increase the UV illuminance in the cavity 410.

In some embodiments, the shell 412 may include an intake 414 for connection to the inlet duct. The diameter of the intake 414 is smaller than the body diameter of the cavity 410 to retain the air in the cavity 410. In some embodiments, the inner column 420 may include a vent 424 on one end of the inner column 420 for connection to the outlet duct. The diameter of the vent 424 is smaller than the body diameter of the cavity 410 to retain the air in the cavity 410. In some embodiments, the intake 414 may be on the side surface of the shell 412 while the vent 424 may be on one end of the inner column 420. In some other embodiments, the intake 414 may be on the inner column 420 while the vent 424 may be on the shell 412.

The UV lamp module 400 includes UV lamps 422 arranged along the inner column 420. When the air flows into the cavity 410, the UV lamps 422 emit the UV rays to sterilize the air in the cavity 410, and the sterilization efficiency of the UV lamp module 400 increases since the air may retain in the cavity 410. The UV lamps 422 may be arranged surrounding the cavity 410 to increase the contacting area of the UV rays and the air. Although only two adjacent UV lamps 422 are illustrated in FIG. 4, other numbers and arrangements of the UV lamps 422 are included in the scope of this disclosure.

In some embodiments, the wavelengths that excite oxygen into ozone may not be included in the UV rays emitted by the UV lamps 422. This prevents the air that leaves the cavity 410 having additional ozone component and causing discomfort of human body, which allows the application of the UV lamp module 400 in the space with human.

Figure 5:
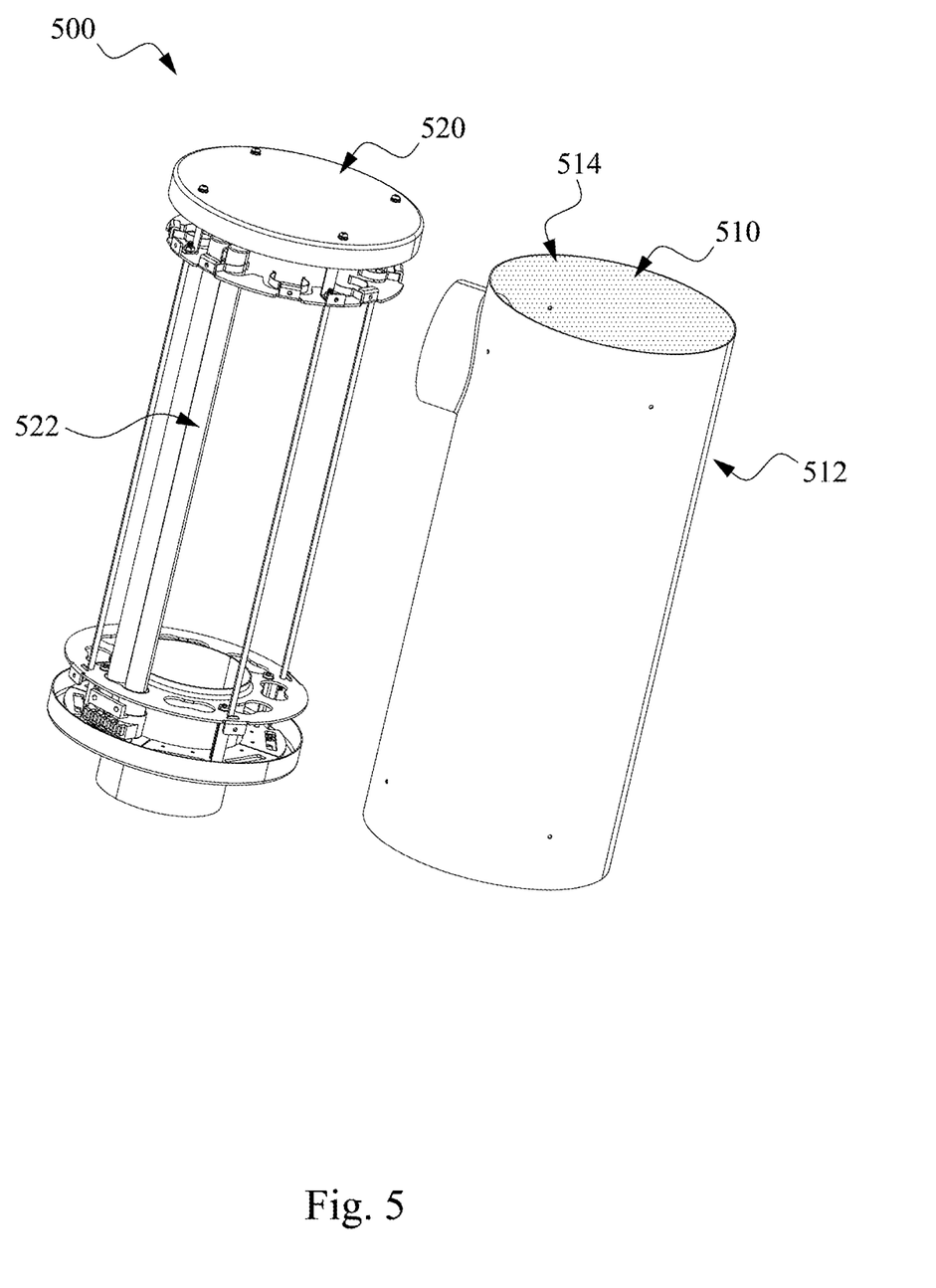

According to some embodiments, FIG. 5 illustrates an exploded view of the UV lamp module 500. The UV lamp module 500 is similar to the UV lamp module 400 in FIG. 4, and the discussion of the similar features would not be repeated. The shell 512 of the UV lamp module 500 further includes a reflector 514.

The reflector 514 is formed on the inner surface of the shell 512 so that the reflector 514 surrounds the inner column 520 and the UV lamps 522. The reflector 514 has high reflectance of the UV rays, which increases the UV rays reflection in the cavity 510, increases the sterilization efficiency in the UV lamp module 500, reduces the necessary numbers of the UV lamps 522 provided by the UV lamp module 500, and extends the service life of the UV lamps 522.

In some embodiments, the reflector 514 may include metal material, such as aluminum. In some embodiments, the reflectance of the reflector 514 may be higher than 85%. The reflector 514 may include the reflective paint coated on the inner surface of the shell 512. In some embodiments, the reflector 514 and the shell 512 may be one-piece formed. In some embodiments which the UV lamps 522 of the inner column 520 are less than the UV lamps 422 in FIG. 4, the UV lamp module 500 may reach the same sterilization efficiency as the UV lamp module 400.

Figure 6:
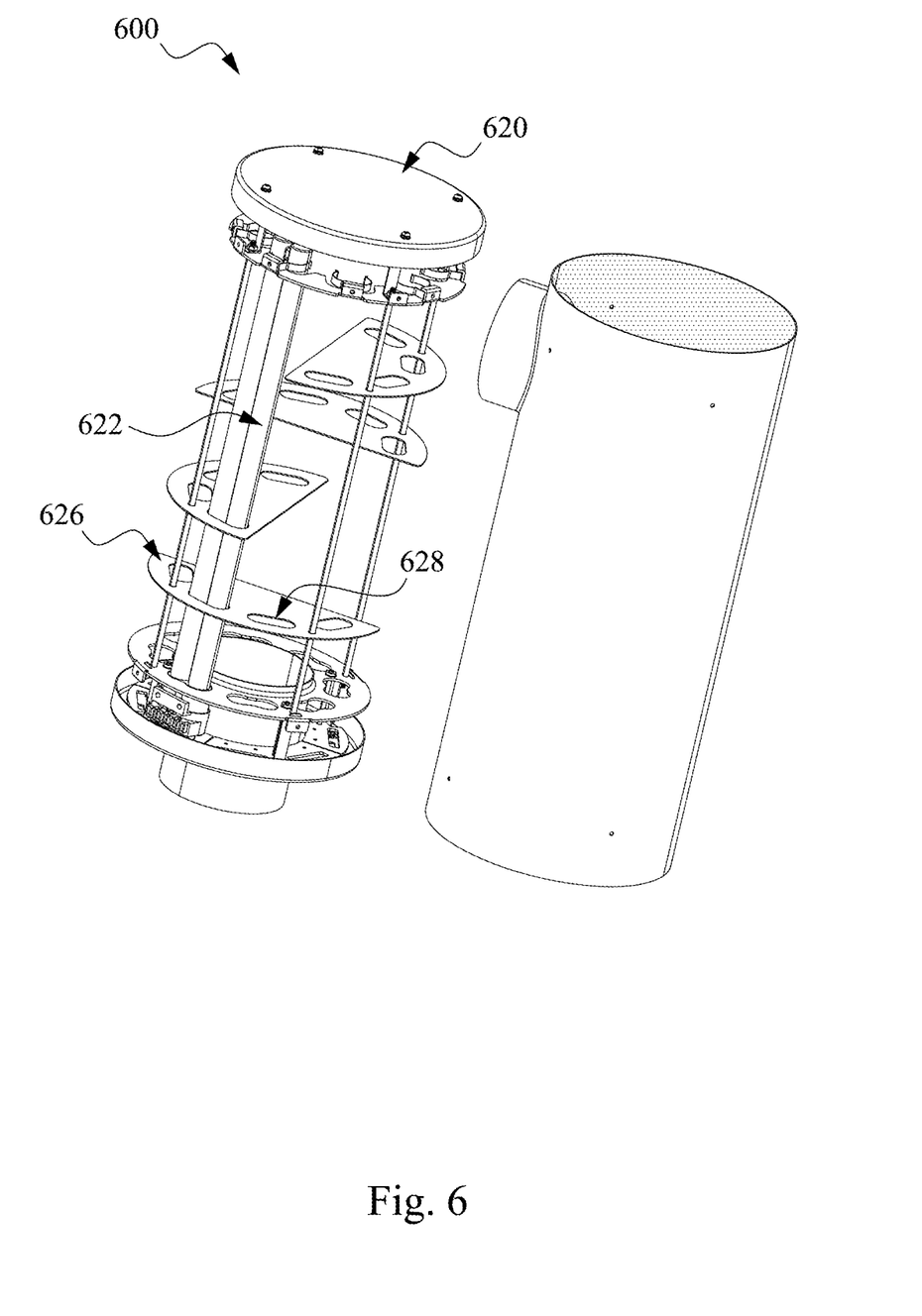

According to some embodiments, FIG. 6 illustrates an exploded view of the UV lamp module 600. The UV lamp module 600 is similar to the UV lamp module 500 in FIG. 5, and the discussion of the similar features would not be repeated. The inner column 620 of the UV lamp module 600 further includes spoilers 626.

The spoilers 626 may uniform the air flowing into the UV lamp module 600, which increases the sterilization efficiency. As shown in FIG. 6, the spoiler 626 includes a semicircle board with holes 628. The UV lamps 622 may be interposed into the holes 628 so that the spoiler 626 would not disturb the arrangement of the UV lamps 622.

A plurality of spoilers 626 may be staggered with different angles, such as rotated 90 degrees, to increase the uniform effect of the spoiler 626. However, it should be noted that the UV lamp modules 600 with other shapes, numbers, and arrangements of the spoilers 626 are included in the scope of this disclosure.

Figure 7:
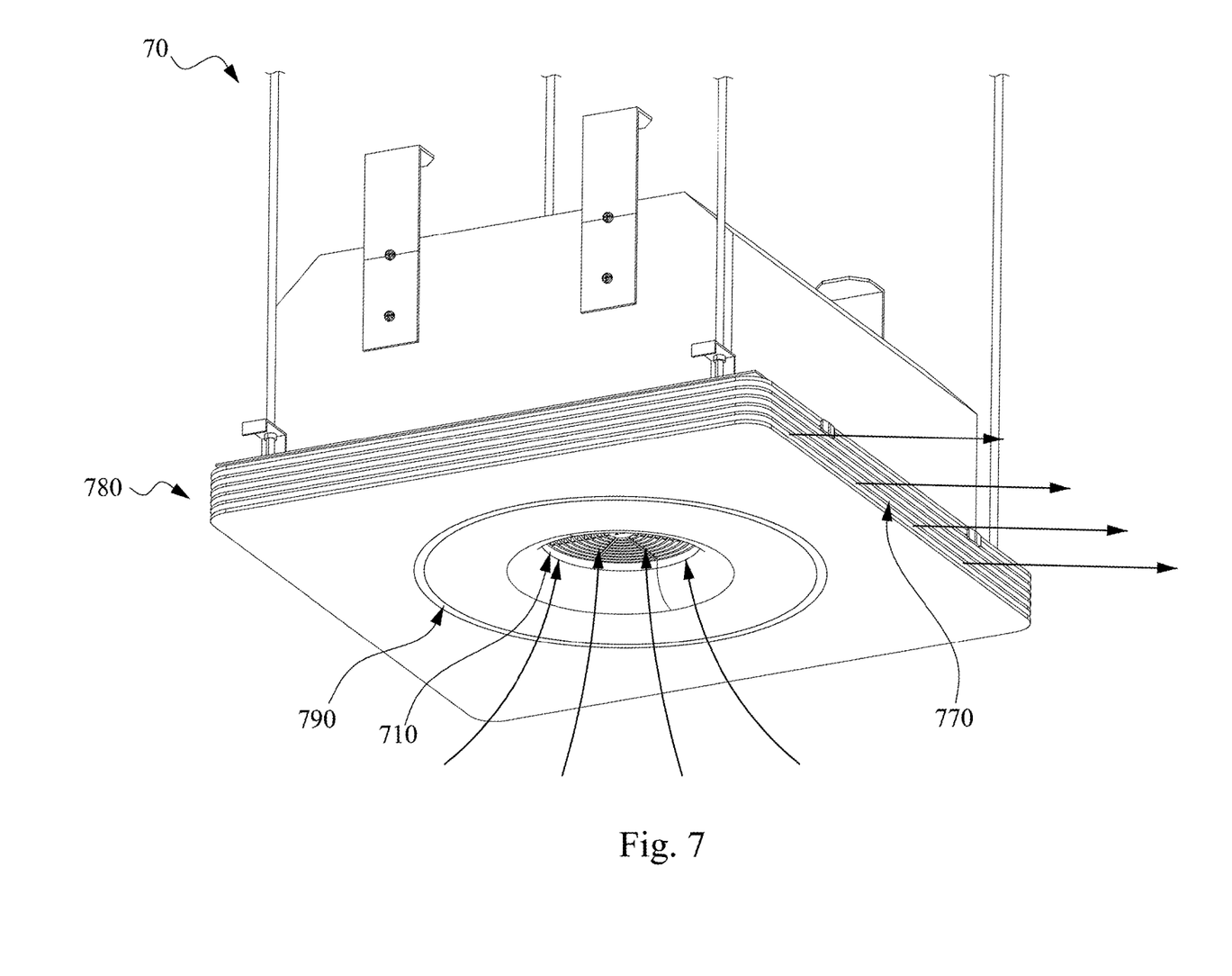
FIG. 7 to FIG. 8 illustrate the air flow direction in the UV germicidal module of the UV air germicidal lamp system in operation according to some embodiments of this disclosure.
Figure 8:
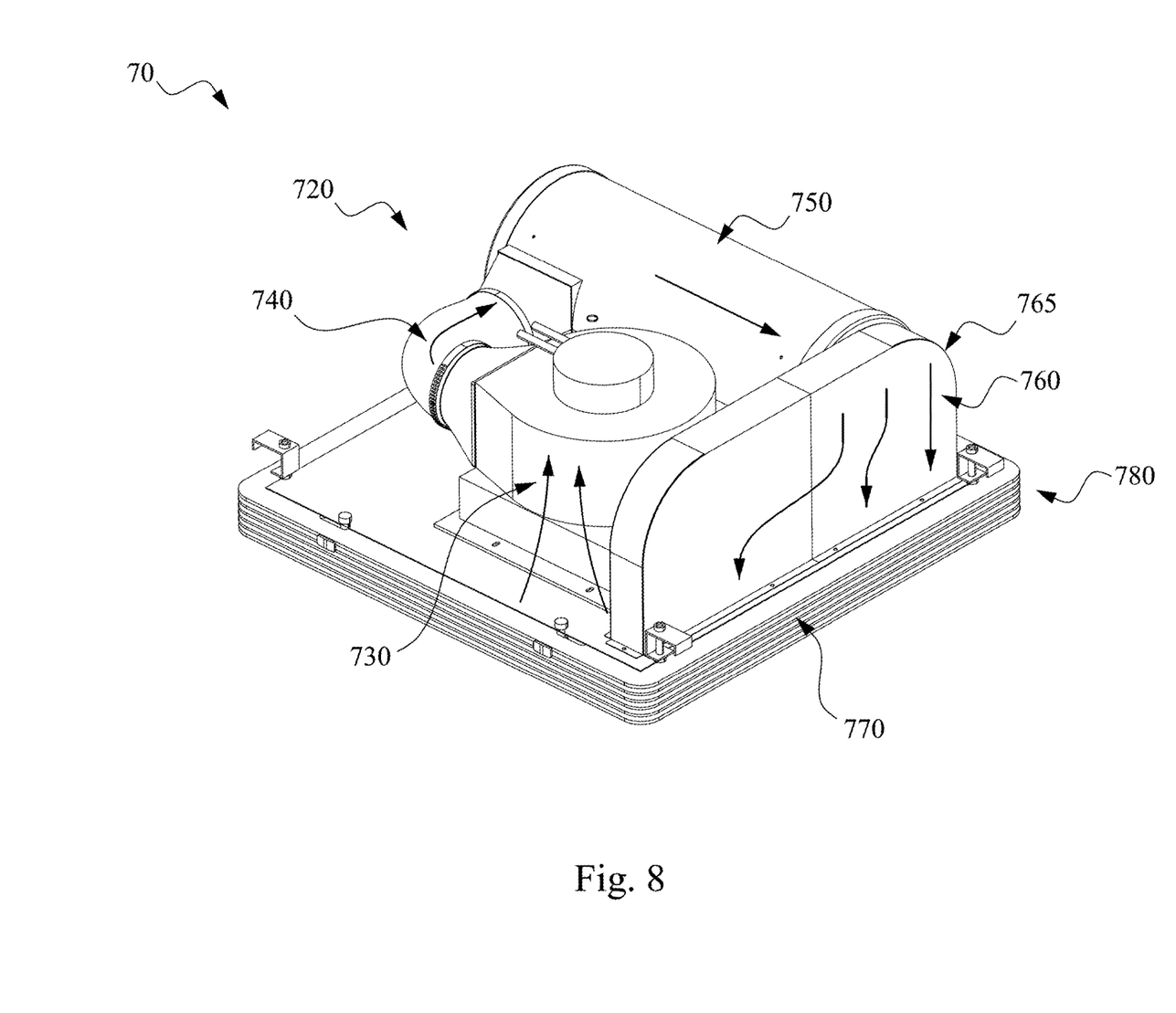

According to some embodiments, FIG. 7 to FIG. 8 illustrate the air flow direction shown by arrows in the UV germicidal module 720 of the UV air germicidal lamp system 70 in operation. The UV air germicidal lamp system 70 is similar to the UV air germicidal lamp system 10 in FIG. 1A and may include various components in the above mentioned embodiments.

Referring to both FIG. 7 and FIG. 8, the air may be driven by the fan 730 and flow into the fan 730 of the UV germicidal module 720 through the air inlet 710. The air inlet 710 may be funnel-shaped to increase the air mount flowing into the UV germicidal module 720. The fan 730 provides a single flow direction and accelerates the air convection in the environment, which improves the sterilization efficiency. The air is then concentrated by the inlet duct 740, sent into the UV lamp module 750, and sterilized by the UV lamp module 750.

As a result of the larger body diameter of the cavity of the UV lamp module 750 compared to the diameter of the intake connecting to the inlet duct 740, the flow speed decreases after the air flows into the UV lamp module 750 through the inlet duct 740. Therefore, the air is retained in the UV lamp module 750, which allows more sufficient sterilization and increases the sterilization efficiency. In some embodiments, the UV lamp module 750 includes the spoiler (not shown) that uniforms the air during sterilization and increases the sterilization efficiency.

The air after sterilization flows to the air outlet 770 through the outlet duct 760 to achieve the air purifying effect. As a result of the larger body diameter of the cavity of the UV lamp module 750 compared to the diameter of the vent connecting to the outlet duct 760, the flow is obstructed when leaving the UV lamp module 750 by the outlet duct 760. Therefore, the air is retained in the UV lamp module 750, which allows more sufficient sterilization and increases the sterilization efficiency.

In some embodiments, the outlet duct 760 may include the fillet 765 on the upper portion so that the air through the outlet duct 760 may be guided to smoothly leave the outlet duct 760. In some embodiments, the outlet duct 760 may include the cross-sectional area parallel to the base frame 780 with an area gradient that gradually reduces from the side adjacent to the base frame 780 along the height direction of the outlet duct 760. This drives the air in the outlet duct 760 to flow toward the air outlet 770.

The two ends of the UV lamp module 750 are respectively connected to the inlet duct 740 and the outlet duct 760, which prevents the leakage of the UV rays in the UV lamp module 750. Therefore, the UV lamp module 750 may be operated without influencing the human body in the space.

The UV air germicidal lamp system 70 includes the air inlet 710 and the air outlet 770 that are not coplanar. This avoids the mixing of the air before and after sterilization so that the possibility of the reinfection of the air after sterilization may be decreased.

The UV air germicidal lamp system 70 includes the UV germicidal module 720 and the lamp module 790 that may operate individually. When the UV germicidal module 720 is working for sterilization, the lamp module 790 may be on-state or off-state. This individual operation mode may reduce the restriction of application. For example, the UV germicidal module 720 of the UV air germicidal lamp system 70 may maintain on-state for continuous sterilization, while the lamp module 790 illuminates when it detects human existing in the space. Therefore, the power consumption may reduce, and the life of the components in the UV air germicidal lamp system 70 may extend.

The UV air germicidal lamp system 70 may be disposed in the ceiling so that the UV air germicidal lamp system 70 does not occupy the space to be sterilized and that the influence to human body is decreased.

The present disclosure provides the UV air germicidal lamp system including the UV germicidal module and the lamp module operating individually. The multi-modules integrated in one system may reduce the necessary space for installation. The UV air germicidal lamp system may be further suspended in the ceiling to reduce the changing of the original layout.

The UV air germicidal lamp system disclosed by the present disclosure includes the UV germicidal module including the fan providing a single flow direction. The fan with the separated air inlet and air outlet of the UV air germicidal lamp system may separate the air before and after sterilization, increase the air convection, and improve the sterilization efficiency. The UV germicidal module also includes the inlet duct, the UV lamp module, and the outlet duct packaging the UV sterilization process in the UV germicidal module so that the air sterilization may be performed in the space with human. The UV lamp module further includes the cavity diameter larger than the diameter of the inlet duct and the outlet duct, which leads to the retention of the air in the UV lamp module and the improvement of the sterilization efficiency.

What is claimed is:

1. An ultraviolet air germicidal lamp system, comprising:
a base frame comprising an air inlet and an air outlet;
an ultraviolet germicidal module on the base frame, wherein the ultraviolet germicidal module comprises:
a fan connected to the air inlet;
an ultraviolet lamp module comprising a cavity with an intake and a vent and a plurality of ultraviolet lamps disposed in the cavity, wherein the ultraviolet lamp module comprises a shell forming the cavity and an inner column in the cavity, and the ultraviolet lamps are arranged along the inner column;
an inlet duct connecting the intake of the cavity and the fan; and
an outlet duct connecting the vent of the cavity and the air outlet, wherein a body diameter of the cavity is larger than a diameter of the intake and a diameter of the vent, and one of the inlet duct and the outlet duct is connected to a side surface of the shell while the other one is connected to the inner column; and
a lamp module disposed in the base frame.

2. The ultraviolet air germicidal lamp system of claim 1, wherein the inlet duct, the ultraviolet lamp module, and the outlet duct are arranged as a spiral shape.

3. The ultraviolet air germicidal lamp system of claim 1, wherein the inlet duct, the ultraviolet lamp module, and the outlet duct are arranged as a linear shape.

4. The ultraviolet air germicidal lamp system of claim 1, wherein the ultraviolet lamp module is disposed between the air inlet and the air outlet.

5. The ultraviolet air germicidal lamp system of claim 1, wherein the air inlet is funnel-shaped.

6. The ultraviolet air germicidal lamp system of claim 1, wherein the fan is a centrifugal fan.

7. The ultraviolet air germicidal lamp system of claim 1, wherein the ultraviolet lamp module further comprises a reflector disposed on an inner surface of the cavity.

8. The ultraviolet air germicidal lamp system of claim 1, wherein the ultraviolet lamp module further comprises a plurality of spoilers disposed in the cavity.

9. The ultraviolet air germicidal lamp system of claim 1, wherein the outlet duct comprises a fillet.

10. The ultraviolet air germicidal lamp system of claim 1, wherein a cross-sectional area of the outlet duct parallel to the base frame gradually reduces from a side adjacent to the base frame.

11. The ultraviolet air germicidal lamp system of claim 1, wherein the air inlet is disposed on a bottom surface of the base frame, and the air outlet is disposed on a side surface of the base frame.

12. The ultraviolet air germicidal lamp system of claim 1, wherein the lamp module and the ultraviolet germicidal module are disposed on opposite sides of the base frame.

13. The ultraviolet air germicidal lamp system of claim 1, wherein the ultraviolet lamp module and the lamp module are individual modules.

14. The ultraviolet air germicidal lamp system of claim 1, further comprising a suspension line connected to the base frame.

15. The ultraviolet air germicidal lamp system of claim 1, further comprising a mounting bracket connected to the base frame.

16. The ultraviolet air germicidal lamp system of claim 1, further comprising a case disposed on the base frame to form a storage space.

17. The ultraviolet air germicidal lamp system of claim 16, further comprising a suspension bracket connected to the case.

18. The ultraviolet air germicidal lamp system of claim 16, wherein the fan, the inlet duct, the ultraviolet lamp module, and the outlet duct are disposed in the storage space.

19. The ultraviolet air germicidal lamp system of claim 16, wherein the fan is disposed in the storage space, and the ultraviolet lamp module and the outlet duct are disposed outside of the storage space.

20. The ultraviolet air germicidal lamp system of claim 16, wherein the ultraviolet germicidal module is disposed outside of the storage space.

* * * * *